(12) United States Patent
Nevo et al.

(10) Patent No.: US 6,871,086 B2
(45) Date of Patent: Mar. 22, 2005

(54) ENDOSCOPIC EXAMINING APPARATUS PARTICULARLY USEFUL IN MRI, A PROBE USEFUL IN SUCH APPARATUS, AND A METHOD OF MAKING SUCH PROBE

(75) Inventors: Erez Nevo, Natanya (IL); Abraham Roth, Kfar Hassidim (IL)

(73) Assignee: Robin Medical Inc., Baltimore, MD (US)

( * ) Notice: Subject to any disclaimer, the term of this patent is extended or adjusted under 35 U.S.C. 154(b) by 0 days.

(21) Appl. No.: 10/394,190

(22) Filed: Mar. 24, 2003

(65) Prior Publication Data

US 2003/0187347 A1 Oct. 2, 2003

Related U.S. Application Data

(63) Continuation-in-part of application No. 09/762,953, filed on Feb. 15, 2001, now Pat. No. 6,516,213.
(60) Provisional application No. 60/367,481, filed on Mar. 27, 2002, and provisional application No. 60/368,561, filed on Apr. 1, 2002.

(51) Int. Cl.$^7$ ................................................. A61B 5/05
(52) U.S. Cl. ...................................... 600/424; 600/410
(58) Field of Search ................................. 600/424, 410, 600/117, 407, 109, 101, 160, 423, 411; 128/897; 606/130; 324/207.13, 207.17, 207.22, 260, 326

(56) References Cited

U.S. PATENT DOCUMENTS

| 4,752,738 A | 6/1988 | Patrick et al. |
|---|---|---|
| 5,035,231 A | 7/1991 | Kubokawa et al. |
| 5,271,400 A * | 12/1993 | Dumoulin et al. .......... 600/410 |
| 5,307,814 A | 5/1994 | Kressel et al. |
| 5,427,103 A | 6/1995 | Fujio et al. |
| 5,500,596 A | 3/1996 | Grist et al. |
| 5,836,869 A | 11/1998 | Kudo et al. |
| 5,964,705 A | 10/1999 | Truwit et al. |
| 5,998,999 A | 12/1999 | Richard et al. |
| 6,263,229 B1 | 7/2001 | Atalar et al. |
| 6,381,485 B1 * | 4/2002 | Hunter et al. ................ 600/407 |
| 6,470,204 B1 * | 10/2002 | Uzgiris et al. ............... 600/411 |
| 6,475,154 B1 | 11/2002 | Wu et al. |
| 6,487,437 B1 | 11/2002 | Viswanathan et al. |
| 6,516,213 B1 | 2/2003 | Nevo |
| 6,628,980 B2 * | 9/2003 | Atalar et al. ................. 600/423 |

OTHER PUBLICATIONS

Schilling et al., "Mucinous cystadenomas and intraductal papillary mucinous tumors of the pancreas in magnetic resonance cholangiopancreatography", *Endoscopy*. Jun. 2000;32(6):472–6. (Abstract).

Bottomley et al, "High resolution intravascular MRI and MRS by using a catheter receiver coil", *Magn Reson Med*. Oct. 1996;36(4):596–605. (Abstract).

Atkin et al, "Long–term risk of colorectal cancer after excision of rectosigmoid adenomas", *N Engl J Med*. Mar. 5, 1992;326(10):658–62. (Abstract).

Bond JH, "The Management of Patients with Colorectal Polyps", found at: http://www.asge.org/gui/clinical_info/updates/cu_colorectal_polyps.asp#sectionII, 1993.

(List continued on next page.)

*Primary Examiner*—Robin Evans
(74) *Attorney, Agent, or Firm*—G.E.Ehrlich Ltd.

(57) ABSTRACT

Endoscopic examining apparatus, particularly useful in MRI, includes a probe movable through the body cavity; a set of tracking coils carried by the probe; and a set of imaging coils carried by the probe. A control system controls the tracking coils to sense and indicate the location and orientation of the probe within the body cavity, and controls the imaging coils to image selected areas within the body cavity. Also described are a novel probe particularly useful in such apparatus, and a novel method of making such probes by a printed circuit technique.

35 Claims, 12 Drawing Sheets

OTHER PUBLICATIONS

Dumoulin et al, "Real–time position monitoring of invasive devices using magnetic resonance", *Magn Reson Med*. Mar. 1993;29(3):411–5. (Abstract).

Feldman et al, "MR endoscopy: preliminary experience in human trials", *Radiology*. Mar. 1997;202(3):868–70. Erratum in: *Radiology* May 1997;203(2):580. (Abstract).

Hildebrandt et al, "Importance of endoscopic ultrasonography staging for treatment of rectal cancer", *Gastrointest Endosc Clin N Am*. Oct. 1995;5(4):843–9. (Abstract).

Hurst et al, "Intravascular (catheter) NMR receiver probe: preliminary design analysis and application to canine iliofemoral imaging", *Magn Reson Med*. Apr. 1992; 24(2):343–57. (Abstract).

Kantor et al, "In vivo 31P nuclear magnetic resonance measurements in canine heart using a catheter–coil", Circ Res. Aug. 1984;55(2):261–6. (Abstract).

Kulling et al, "Local staging of anal and distal colorectal tumors with the magnetic resonance endoscope", *Gastrointest Endosc*. Feb. 1998;47(2):172–8. (Abstract).

Kulling et al, "Local staging of esophageal cancer using endoscopic magnetic resonance imaging: prospective comparison with endoscopic ultrasound", *Endoscopy*. Nov. 1998;30(9):745–9. (Abstract).

Lotfi et al, "Colorectal polyps and the risk of subsequent carcinoma", *Mayo Clin Proc*. May 1986;61(5):337–43. (Abstract).

Martin et al, "Intravascular MR imaging in a porcine animal model", *Magn Reson Med*. Aug. 1994;32(2):224–9. (Abstract).

Martin et al, "MR imaging of blood vessels with an intravascular coil", *J Magn Reson Imaging*. Jul.–Aug. 1992;2(4):421–9. (Abstract).

Richter et al, "Ultrafast magnetic resonance tomography changes the standard in pancreas diagnosis," *Chirurg*. Jun. 2001;72(6):697–703. German. (Abstract).

Rosch et al, "Localization of pancreatic endocrine tumors by endoscopic ultrasonography", *N Engl J Med*. Jun. 25, 1992;326(26):1721–6. (Abstract).

Wiersema et al, "Combined endosonography and fine–needle aspiration cytology in the evaluation of gastrointestinal lesions", Gastrointest Endosc. Mar.–Apr. 1994;40(2 Pt 1):199–206. (Abstract).

Yamada et al, "Early gastric carcinoma: evaluation with high–spatial–resolution MR imaging in vitro", *Radiology*. Jul. 2000;220(1):115–21.

* cited by examiner

ENDOSCOPIC EXAMINING APPARATUS PARTICULARLY USEFUL IN MRI, A PROBE USEFUL IN SUCH APPARATUS, AND A METHOD OF MAKING SUCH PROBE

RELATED APPLICATIONS

The present application includes the subject matter, and claims the priority dates, of Provisional Application No. 60/367,481 filed Mar. 27, 2002, and Provisional Application No. 60/368,561, filed Apr. 1, 2002, the contents which provisional applications are incorporated herein by reference. The present application is also a continuation-in-part of U.S. patent application Ser. No. 09/762,953 filed on Feb. 15, 2001, which issued as U.S. Pat. No. 6,516,213 on Feb. 4, 2003, and incorporates herein by reference the entire disclosure of that patent application.

FIELD AND BACKGROUND OF THE INVENTION

The present invention relates to endoscopic examining apparatus, to a probe useful in such apparatus, and to a method of making an electrical coil assembly useful in such a probe. The invention is particularly useful in an endoscope in MRI (magnetic resonance imaging) apparatus, and is therefore described below with respect to this application, although it will be appreciated that various aspects of the invention could advantageously be used in other applications as well.

Gastrointestinal Endoscopy:

Endoscopy is a common minimally invasive diagnostic and therapeutic procedure. Insertion of endoscopes into a body cavity or lumen (e.g., the gastro-intestinal tract, the genito-urinary system, the brain ventricles), or produced cavity or lumen (e.g. by laparoscopy) enables access to internal organs for visual inspection, for tissue sampling (biopsy), and for management of pathologies. A limiting factor in the use of endoscopes for minimally invasive management of lesions is the ability to determine the invasiveness of the lesion. The decision to perform an endoscopic resection of a lesion may be guided by the gross anatomy of the lesion (for example the shape and the size), or by using imaging modalities like ultrasound at the tip of the endoscope. However, with many lesions, a biopsy is taken and the lesion is subsequently managed, depending on the result of the biopsy, by open surgery or by additional endoscopy.

Colorectal cancer is the second most common visceral malignancy in the United States. More than 160,000 new cases are diagnosed each year; the disease causes approximately 60,000 deaths; and the lifetime average incidence for each individual is 6% (Bond, 1993). The two most effective ways to reduce the high mortality rate associated with this cancer are to diagnose it at an early stage, or to prevent it by detecting and resecting the precursor lesion of most of these cancers, the neoplastic adenoma (Atkin et al., 1993). Recent data, including results from the National Polyp Study (Winawer et al., 1991), support this claim and show that screening reduces colorectal cancer and saves lives. Polyps of the large bowel are very common and occur in more than 30% of people living in Western countries. More than 650,000 patients currently undergo colonoscopic polypectomy each year in the United States. Approximately 70% of polyps removed at the time of colonoscopy are true neoplastic growths or adenomas. When a small polyp is detected during screening proctosigmoidoscopy, a biopsy of the polyp should be performed to determine if it is an adenoma.

The finding of a left colonic adenoma is an indication for colonoscopy to resect the polyp and search for additional synchronous lesions, since the incidence of synchronous adenomas is 40% to 50% (Winawer et al., 1997). Most patients with one or more polyps diagnosed by barium enema examinations should be offered colonoscopy to resect the detected polyps and to clear the colon of other lesions that might have been missed by the diagnostic X-Ray study (Hogan et al., 1977). Large sessile polyps almost always contain villous tissue with appreciable premalignant potential, and they tend to recur locally after colonoscopic resection. In many cases it is not clear whether these polyps can be safely or completely excised endoscopically, and the patients are referred for surgical resection. In some cases a polyp that appears benign at the time of colonoscopic polypectomy is later diagnosed by pathologic examination as a malignant polyp since it contains malignant cells that penetrate deep into the wall.

It is clear from the above that the use of local imaging can greatly improve the yield of endoscopy by better distinguishing between resectable and non-resectable lesions.

Endoscopic Ultrasound:

Endoscopic ultrasound (EUS) was introduced more than 20 years ago and is currently offered by major manufacturers of endoscopes (e.g. EVIS 130 ultrasonic videoscope, Olympus, Japan). Using EUS with mid-range frequencies (7.5 to 20 MHZ) enables the wall of the GI tract to be imaged as a five to nine layer structure of alternating bright (echogenic) and dark bands. These image layers largely correspond to the four histologic layers of the wall of the GI tract, but the redundant echo-related, non-histologic layers may cause mis-evaluation of the depth of tumor invasion (e.g. in the gastric wall, Yamada et al., 2001). Yet, the ease of using EUS, and its ability to distinguish between solid and nonsolid (e.g. cystic) structures, indicates its use for the following clinical indications:

1. Submucosal Abnormalities: EUS can be used to determine whether an abnormality is extrinsic (compression by normal organs or disease with all wall layers intact) or intramural. Basic distinctions can be made as to whether the tumor is cystic, vascular, or solid. It must be understood, however, that a precise histologic diagnosis, and the differentiation between benign and malignant tumors, are not possible with EUS imaging.

2. Cancer Staging: Diagnosis of cancer depends primarily on histologic or cytologic evaluation of biopsies. EUS cannot be reliably used to differentiate benign from malignant lesions, for example benign and malignant gastric ulcers. On the one hand, EUS was used to stage cancer of the esophagus, stomach, colon, and rectum (Tio, 1995). With the TNM staging classification, EUS images of the GI tract wall can be used to define the depth of tumor invasion (T), and in some cases involvement of regional lymph nodes (N). On the other hand, high-frequency EUS has a short depth of field and is not a good test for staging distant metastases (M). For staging the depth of tumor invasion of esophageal, gastric, and colorectal cancer, EUS has shown preoperative accuracy in the 80% to 90% compared with surgical pathology, while accuracy of staging regional lymph node metastases has been in the range of 70% to 80%.

This staging information can be used to determine wide operative resection, local endoscopic excision, non-operative management, adding preoperative adjuvant chemotherapy or radiation therapy (Lightdale, 1999; Hildebrandt and Feifel 1995). Lesions confined to the mucosa in patients who have increased operative risk may be treated endoscopically with various ablation modalities. Subepithelial lesions in the deep mucosa or small lesions in the submucosa can be removed during endoscopy if their location and size can be confirmed with EUS (Lightdale, 1996; Tada et al., 1996). Body imaging with CT or MRI of the chest and abdomen is usually the next step in staging the anatomic extent of GI cancers. The management of the cancer (i.e. by endoscopy, surgery, radiation, chemotherapy) is determined by the results of the endoscopy and body imaging, so the quality of local and body imaging plays a critical role in the management of these patients. MRI-enhanced endoscopy, providing high quality local as well as body images, can become the optimal tool for the initial management of these patients.

3. Endoscopic Needle Aspiration: EUS-guided fine-needle aspiration for cytology has been developed in an effort to improve the diagnosis of submucosal lesions, lymph nodes, and pancreatic masses (Wiersema et al., 1994). The initial experience indicates that this may be helpful in cancer staging, particularly in lymph node staging of non-small-cell lung cancer and in documenting pancreatic cancer. The overall complication rate from endoscopic fine-needle puncture is less than 1%. Experience is small, but the procedure seems at least comparable and in some cases more effective than CT-guided techniques for this purpose (Wiersema et al., 1994). MRI, with its superior soft-tissue contrast compared with ultrasound and CT, and its unique capability of scanning in any location and orientation, may become the modality of choice to guide fine-needle aspiration during endoscopy.

4. Pancreatic and Biliary Disease: EUS has been used to detect cysts, adenocarcinomas, and islet cell tumors of the pancreas. Lesions as small as 5 to 10 mm have been localized (Röosch et al., 1992). EUS-guided fine-needle aspiration has been used successfully to obtain material for cytology and tumor markers and to guide internal drainage of pancreatic pseudocysts. Staging of advanced pancreatic cancer can be achieved with accuracy in the 85% range. Ampullary tumors can also be staged, allowing endoscopic removal of ampullary adenomas in patients at high surgical risk. In severe pancreatitis, EUS is limited in its ability to differentiate between inflammation and neoplasm. Furthermore, early pancreatic structural changes cannot be detected by EUS in cases where other tests of pancreatic function and structure are normal.

Advantages of MRI:

Many of the advantages of MRI that make it a powerful clinical imaging tool are also valuable during interventional procedures. The most significant ones are the superior soft-tissue contrast, compared with all other imaging modalities, which allows for detection of early malignant growth; lack of ionizing radiation which enables its use for long, complex procedures; and its unique oblique and multiplanar imaging capabilities which enable the imaging of any plane or volume in the body, including non-planar surfaces. Its traditional drawbacks—high cost, slow imaging, and claustrophobic environment—are being eliminated through the introduction of relatively low-cost, fast, open scanners. These unique advantages make MRI a suitable imaging modality to enhance optical endoscopy.

Specifically, endoscopic MRI (EMRI) is not limited by some of the limitations of EUS mentioned above: The better soft-tissue contrast and the higher resolution may provide better correlation between imaging and histology. This is nicely demonstrated by a recent study that compared in-vitro MR scans using a small receiving coil and histologic sections in the diagnosis of specimens with suspected early gastric carcinoma (Yamada et al., 2001). While EUS is limited in its ability to differentiate between different pancreatic pathologies, for example chronic pancreatitis and pancreatic cancer, standard diagnostic MR scans are being proposed for the diagnosis of pancreatic cancer (Richter et al., 2001; Albert et al., 2000).

It should be noted that EUS is easier to perform as part of a standard endoscopy procedure, while EMRI requires the use of an MR-compatible endoscope and MR-scanner. However, unlike EUS, the combined use of high-resolution local scan with whole body scan is easily accomplished in standard MR scanners and may provide a "one shop" modality for comprehensive TNM (Tumor—Node—Metastase) cancer staging of different organs.

Intraluminal MRI

The use of intraluminal coils for MR studies dates back to 1984, when Kantor and colleagues used a catheter MR probe for in-vivo 31P MR measurements in the canine heart. Hurst and colleagues (1992) used simulation and experimentation to compare several configurations for intravascular MR receiver probes. They showed that optimal receiving sensitivity can be achieved by an opposed-coil configuration. The design is based on two coils, separated by a gap region, whose magnetic fields are in opposition to one another. The region between the two coils experiences a large magnetic flux and therefore achieves high sensitivity to regions between the coils and external to the diameter of the coils. Martin and Henkelman (1994) used similar configuration with an external diameter of 3.5 mm and a separation of 7.3 mm and achieved good receiving sensitivity up to a depth of 10–20 mm. This opposed-coil configuration has best performance when the coils lie parallel to the direction of the static magnetic field. However, it cannot be used when the coils are transverse to the direction of the static field, since the RF field has zero component in this direction. As most endoscopy procedures are done in organs with different spatial orientation inside the body, other types of RF probes with a full spherical coverage must be used.

Atalar and colleagues (1996) proposed the combination of two orthogonal coils (a quadrature coil design) to achieve better spatial coverage of the probe. They also proposed the use of printed circuit technology to manufacture low cost probes (U.S. Pat. No. 6,263,229). This arrangement eliminates the need to align the pickup coil along the main magnetic field of the magnetic resonance scanner. Kulling et al. (1997) tested similar configuration and demonstrated a good coverage around the endoscope. The quadrature coil design is useful to image slender lumen like blood vessels and provides adequate sensitivity in the radial direction around the probe, but poor longitudinal sensitivity and no "looking forward" capabilities.

Pioneering studies with EMRI have been published during recent years. Feldman et al. (1997) performed local staging of esophageal and rectal cancer (without pathologic correlation) using an MR-compatible endoscope with embedded receive-only MR coil. Kulling and colleagues (two studies published in 1998) found EMRI to be comparable to EUS for local staging of esophageal cancer in one study and of anal and distal colorectal tumors in the second study, but indicated more than 25% failure due to motion artifacts in the first study.

None of the published studies with intraluminal MRI used tracking since only optical tracking, which cannot be used with endoscopes, is commercially available for some open MR scanners. However, tracking is critical for optimal use of high resolution, local MR imaging, by enabling realtime prescription of the image plane. The EndoScout, described below, provides an optimal solution for MR tracking which is compatible for use with endoscopes.

The MRI Tracking System of U.S. Pat. No. 6,516,213

U.S. Pat. No. 6,516,213, cited above and incorporated in its entirety herein by reference, discloses a new tracking system which extends the existing limitations of MR tracking and provides an optimal tool for interventional MRI. Rather than using a tracking system based on external reference transmitters, the new tracking system uses electromagnetic fields that are generated by the MR scanner. A basic feature of MRI is the spatial encoding of the RF signal emitted from tissue protons by the spatially variable magnetic fields of the gradient coils of the scanner. The miniature sensors in the new tracking system measure the gradient magnetic fields; and the sensor's location and orientation are determined by comparing the measured fields to the known fields of the scanner.

The new MRI tracking system has significant advantages over existing ones. It can be easily used with any MR scanner as a "plug and play" option; there is no need for any mechanical integration (as needed with the Flashpoint optical system), electromagnetic adaptation, or change in the normal mode of operation of the scanner (as needed with General Electrics MR-Tracking technology, Dumoulin et al., 1993). Unlike other electromagnetic tracking methodologies that are used with other imaging modalities (e.g. the Carto system for X-ray catheterization, Biosense-Webster, Inc., Diamond Bar, Calif.; US-Guide and CT-Guide, UltraGuide Inc., Lakewood, Colo.) the new technique described in Pat. No. 6,516,213 is totally passive. It does not require any excitation of the sensors, nor the use of dedicated electromagnetic reference fields. Since the same spatial encoding mechanism is used by the scanner to reconstruct the image, and by the tracking system to determine the location of the sensor, there is no need to align different coordinate systems. In contrast to currently used optical tracking, the above new technique does not need an unobstructed line of sight to track the device (thus it can track non-rigid surgical tools and intra-body devices like catheters and endoscopes). It requires only one sensor to provide tracking of position and orientation, while competing tracking technologies (the Flashpoint, the MR-Tracking) determine only the location and thus require the use of at least two rigidly connected sensors to determine the device orientation.

OBJECTS AND BRIEF SUMMARY OF THE INVENTION

An object of the present invention is to provide endoscopic examining apparatus, particularly MRI apparatus, having an integrated imaging and tracking capability. Another object of the present invention is to provide a probe particularly useful in such apparatus; and a further object of the invention is to provide a method of making an electrical coil assembly particularly useful in making such a probe.

According to one aspect of the present invention, there is provided endoscopic examining apparatus for examining the interior of a body cavity, comprising: a probe movable through the body cavity; a coil assembly including a plurality of coils carried by the probe; and a control system for controlling coils in said assembly to sense and indicate the location and orientation of the probe within the body cavity, and also to image selected areas within the body cavity.

In the preferred embodiment of the invention described below, the coil assembly includes a set of imaging coils and a separate set of tracking coils. The control system controls the set of tracking coils to sense and indicate the location and orientation of the probe within the body cavity, and controls the set of imaging coils to image selective areas within the body cavity.

According to another aspect of the present invention, there is provided MRI apparatus for examining the interior of a body cavity, comprising: means for providing a main magnetic field through the body cavity to be examined; a plurality of gradient coils for generating gradient electromagnetic fields with the body cavity; a probe movable through the body cavity and carrying a set of tracking coils and a set of imaging coils; and a control system for controlling: (a) the gradient coils to generate the gradient electromagnetic fields; (b) the probe tracking coils to sense and indicate the location and orientation of the probe within the body cavity; and (c) the probe imaging coils to image selected areas within the body cavity.

According to a further aspect of the invention, there is provided a probe movable within a body cavity for examining the interior of selected areas thereof; the probe comprising: a set of tracking coils constructed and oriented on the probe to sense the location and orientation of the probe when moved within the body cavity; and a set of imaging coils constructed and oriented to image selected areas within the body cavity.

According to yet another aspect of the present invention, there is provided a method of making an electrical coil assembly, particularly useful for making probes of MRI apparatus, for purposes of examining selected areas of a body cavity, the method comprising: depositing on a planar dielectric substrate a plurality of electrically-conductive deposits in the shape of electrical coils extending parallel to each other along one orthogonal axis of the substrate and spaced from each other along the other orthogonal axis of the substrate; forming the planar dielectric substrate into an annular shape; and joining the opposite edges of the substrate to each other; the plurality of electrically-conductive deposits being configured and located on the planar dielectric substrate such that when the planar dielectric substrate is formed into the annular shape and its opposite ends joined to each other, the plurality of electrically-conductive deposits defined at least two orthogonal electrical coils.

As will be described more particularly below, the invention enables attaining one or more of the following advantages:

1. The combination of a tracking sensor with intraluminal imaging coils enables interactive scan prescription at the location and orientation of the tracking sensor. The user, with a field of view centered at the tip of the endoscope, can get MR images referenced to the same point of view.

2. The use of existing, realtime tracking technology specifically adapted to MRI facilitates the clinical use of the technology with a wide range of MR scanners.

3. The integration of imaging coils to the existing 3D configuration of the tracking sensor provides spherical sensitivity around the tip, and enables imaging in any direction with minimal sensitivity to the direction of the endoscope with respect to the scanner static magnetic field.

4. The whole-body imaging capabilities of the MR scanner and the realtime tracking enable the use of the MR images as a "road map" to rapidly gain access to a lesion previously identified with standard diagnostic MRI.

5. The whole-body imaging can be integrated with the local high-resolution images to provide a comprehensive tool for TNM staging of various cancers.

6. The invention also enables the probe to have a hollow construction to thereby define a passageway for the insertion of a guidewire, for injection of contrast material, for removal of a tissue sample (biopsy), or for other diagnostic or interventional procedure that may be required.

Further features and advantages of the invention will be apparent from the description below.

BRIEF DESCRIPTION OF THE DRAWINGS

The invention is described herein, by way of example only, with reference to the accompanying drawings, wherein.

It is to be understood that the foregoing drawings, and the description below, are provided primarily for purposes of facilitating understanding the conceptual aspects of the invention and various possible embodiments thereof, including what is presently considered to be a preferred embodiment. In the interest of clarity and brevity, no attempt is made to provide more details than necessary to enable one skilled in the art, using routine skill and design, to understand and practice the described invention. It is to be further understood that the embodiments described are for purposes of example only, and that the invention is capable of being embodied in other forms and applications than described herein.

DESCRIPTION OF PREFERRED EMBODIMENTS

Overall Apparatus

Figure 1:
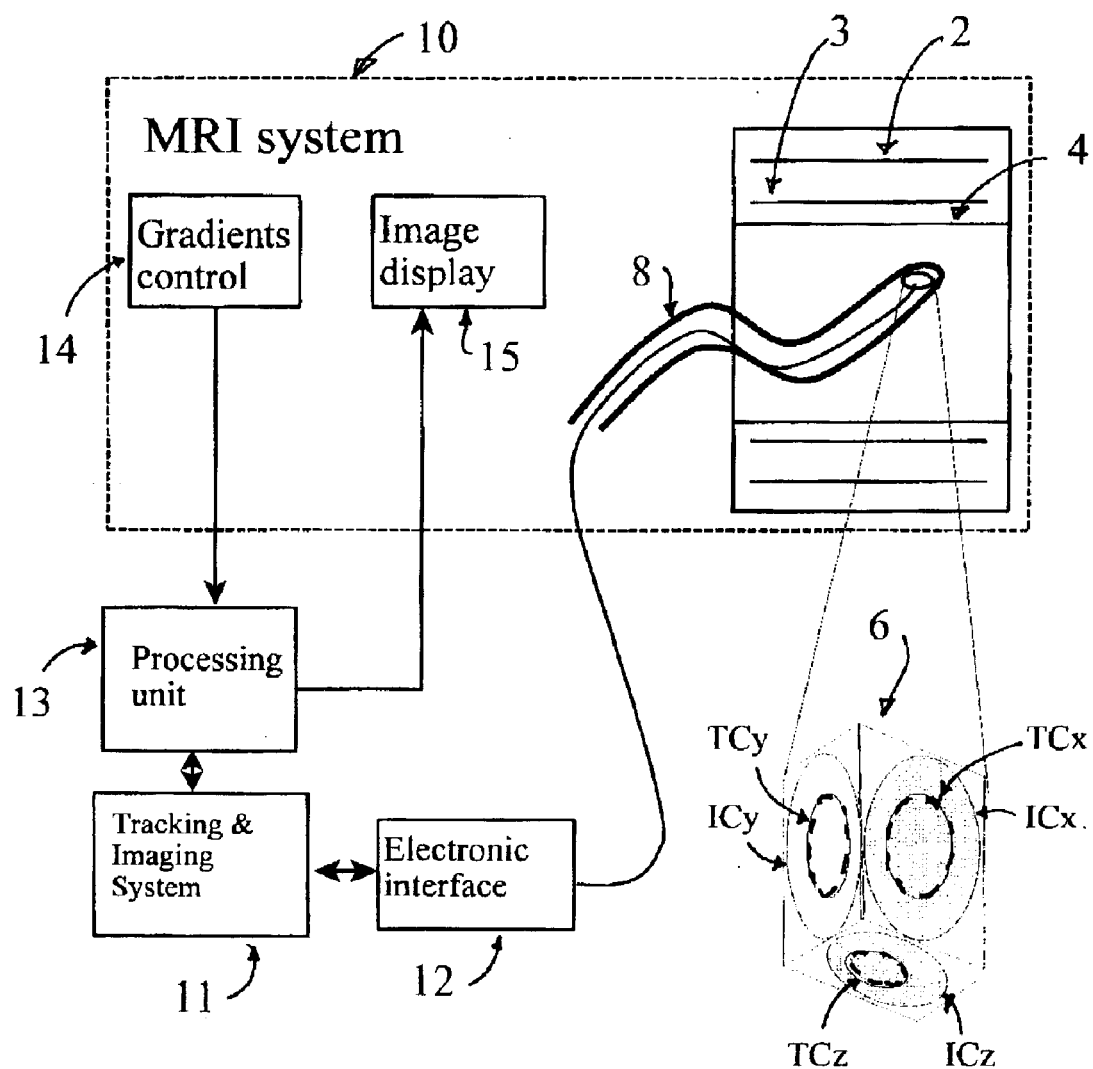
FIG. 1 is a schematic diagram of one form of MRI apparatus constructed in accordance with the present invention.

The apparatus illustrated in FIG. 1 is basically the MRI apparatus described in the above-cited U.S. Pat. No. 6,516,213. Such apparatus includes a main coil for generating a main magnetic field, a plurality of gradient coils for generating gradient electromagnetic fields, and a probe movable through the body cavity and carrying a set of tracking coils for indicating the instantaneously location and orientation of the probe by sensing the instantaneous values of the magnetic fields generated by the gradient coils. The apparatus illustrated in FIG. 1, however, has been modified to import to it the capability of imaging selected areas of the body cavity, by providing the probe with a plurality of imaging coils controlled by the control system of the MRI apparatus.

More particularly, the MRI apparatus illustrated in FIG. 1 includes a main electromagnetic coil schematically designated 2, for generating a main magnetic field; a transmit RF coil 3; and a plurality of gradient coils 4 for generating gradient electromagnetic fields; a probe 6 movable via a catheter 8 through the body cavity or lumen to be examined; and a control system, generally designated 10. As in the MRI apparatus of the above-cited U.S. Pat. No. 6,516,213, the probe carries a set of tracking coils, schematically designated $TC_X$–$TC_Z$, effective to sense the instantaneous magnetic field, which information is processed, together with the known magnitude and direction of the magnetic fields produced by the gradient coils 2, to compute the instantaneous location and orientation of the probe. In this case, however, probe 6 also includes a set of imaging coils, schematically designated $IC_X$–$IC_Z$, which are controlled to image selected areas within the body cavity examined by the probe.

Control system 10 illustrated in FIG. 1 thus also includes a tracking and imaging sub-system 11 for controlling, via an electronic interface 12, the tracking coils $TC_X$–$TC_Z$ and the imaging coils $IC_X$–$IC_Z$ carried by the probe 6. Control system 10 further includes a processing unit 13 controlling the tracking and imaging sub-system 11 and also controlling the gradient-generating coils 4, the RF coil 3, and as well as the main coil 2, via a control unit 14. Processing unit 13 further controls an image display unit 15 for displaying the image generated by the image coils $IC_X$–$IC_Z$ carried by the probe 6, as well as the instantaneous location and orientation of the probe as sensed by the tracking coils $TC_X$–$TC_Z$.

Further information as to the structure and mode of operation of the MRI system illustrated in FIG. 1, except for the imaging coils $IC_X$–$IC_Z$ and their controls, is available in the above-cited U.S. Pat. No. 6,516,213, the entire disclosure of which is incorporated herein by reference for this purpose.

Figure 2:
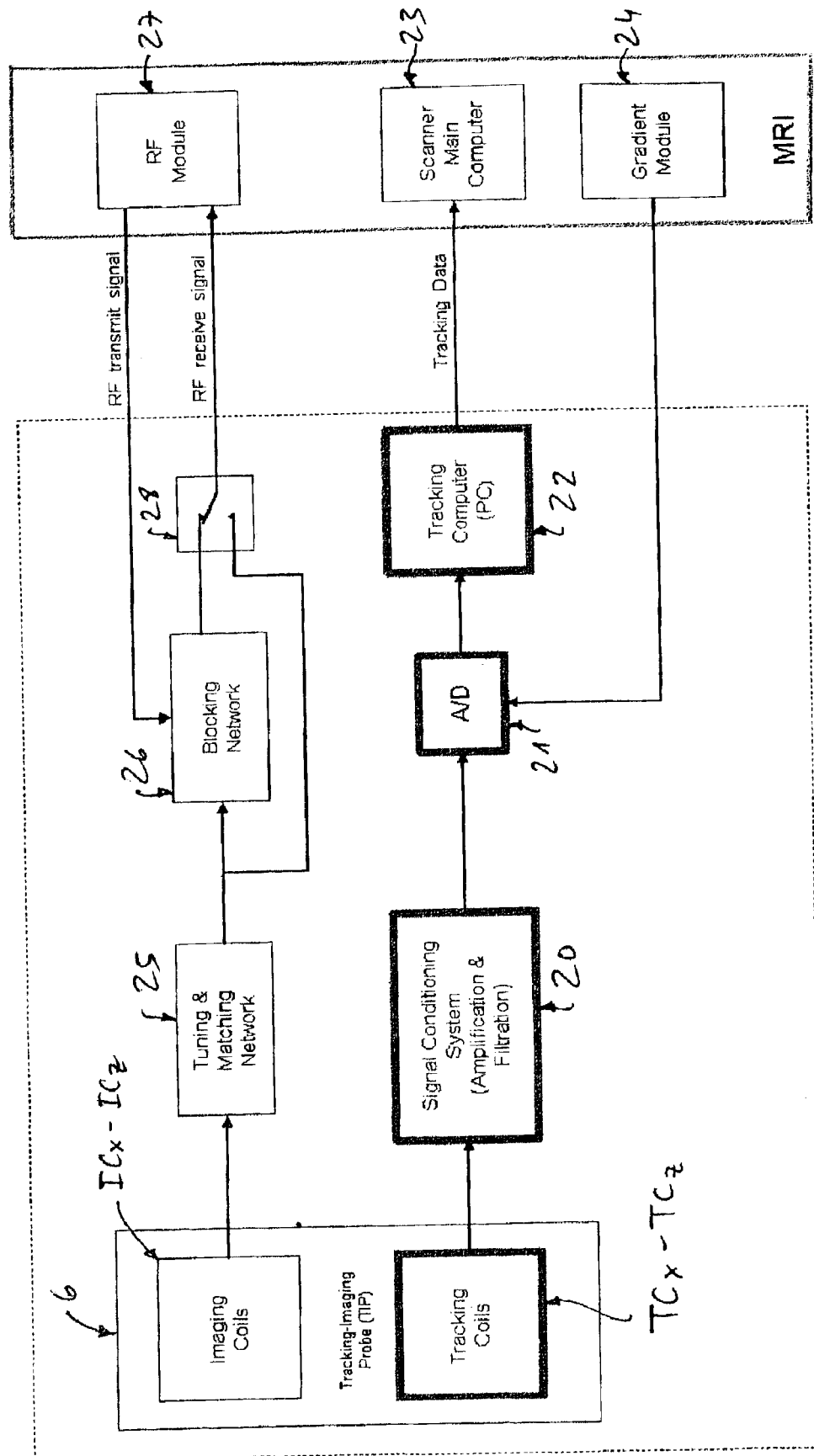
FIG. 2 is a block diagram illustrating the tracking and imaging system in the apparatus of FIG. 1.

The tracking and imaging system 11 illustrated in FIG. 1 is more particularly shown in FIG. 2. As shown, the tracking coils $TC_X$–$TC_Z$ of the probe 6 are electrically connected to a signal conditioning sub-system 20 which performs amplification and filtration functions with respect to the signals sensed by the tracking coils. These signals are converted to digital form by an A/D converter 21 before being fed into a tracking computer 22 to provide tracking data to a scanner main computer 23. Data regarding the instantaneous magnetic field generated by the gradient coils (4, FIG. 1) is also inputted from granted module 24 into the tracking computer 22 via A/D converter 21 and is used by the scanner main computer 23 for computing the instantaneous location and orientation of the probe in the manner described in the above-cited U.S. Pat. No. 6,516,213.

As further shown in FIG. 2, the output from the imaging coils $IC_X$–$IC_Z$ of the probe 6 is fed, via a tuning and matching network 25 and a blocking network 26, to an RF module 27 within the MRI system. The latter networks are illustrated in FIG. 3.

Figure 3:
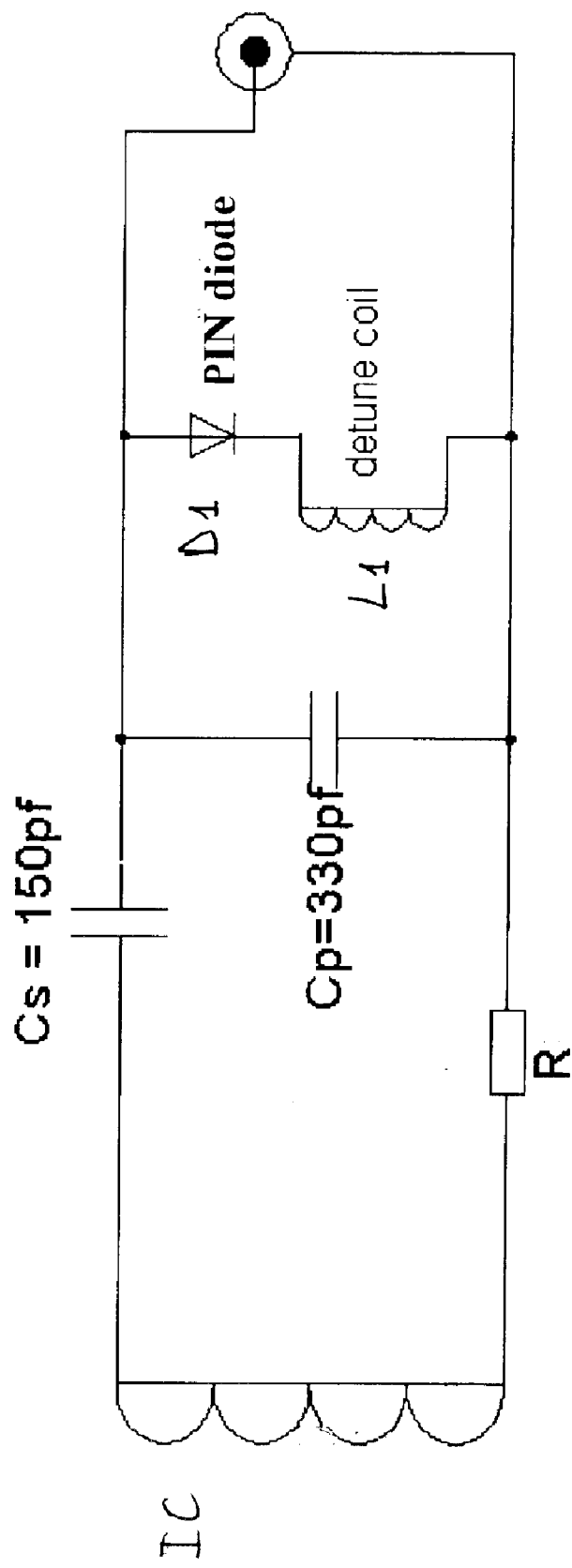
FIG. 3 illustrates an example of the tuning and matching network in the block diagram of FIG. 2.

Thus, each of the imaging coils $IC_X$–$IC_Z$ indicated as IC in FIG. 3, has a resistance (R) and an inductance (L) that depends on the coil's shape, size and surrounding media (e.g. air, water, tissue). In order to tune the circuit to the Larmor frequency of the scanner and to match it to the standard input impedance of the scanner (50 Ohms), two capacitors, one in series ($C_s$) and one in parallel ($C_p$), are added to the coil. FIG. 3 includes a schematic diagram of the RF imaging coil IC and illustrative values for the matching and tuning capacitors $C_S$, $C_P$.

For each coil IC, specific capacitors provide optimal tuning and impedance matching. The determination of the optimal capacitance values for a given coil and operating media may be done theoretically, numerically, or experimentally. For the circuit shown in FIG. 3, the resonance frequency of interest (ω) is given by:

$$\omega = \sqrt{[(Cp + Cs)/L * Cp * Cs)]} \quad (1)$$

and the input impedance (Z(ω)) of the circuit is given by the complex expression:

$$Z(\omega)=1/(\omega*Cp*i+1/(\omega*L*i+1/(\omega*Cs*i)+R)) \quad (2)$$

Equating the resonance frequency ω to the Larmor frequency of the scanner (e.g. 21.3 MHz for a 0.5 Tesla scanner), and the input impedance Z(ω) to 50 Ohms, provides a set of two equations for the two unknown capacitors. The illustrative values in FIG. 3 are based on a numerical analysis made to calculate coarse capacitance values that satisfy these two requirements. This was followed by the use of a function generator and an oscilloscope, to indirectly monitor the resonance frequency and the input impedance, and to fine-tune the capacitor values. A network analyzer can be used to simultaneously measure the resonance frequency and the input impedance of the prototype circuit illustrated in FIG. 3 and to facilitate this selection of the required circuit parameters.

As the working media for the coil may change from person to person, a mechanism for final adjustment of the coil properties is needed. A fine-tuning circuit with variable capacitors may be used to maximize the power received by the coil when an external RF coil 3 of the MR scanner transmits RF signals. Additional tuning can be done by the pre-scan protocol of the scanner that adjusts the frequency of the transmitted RF in order to maximize the received signal.

The blocking network 26 shown in FIG. 3 is controlled to block the respective imaging coil $IC_X$–$IC_Z$ during RF transmit. Thus, the MR scan mechanism requires an RF excitation of the tissue, followed by detection of the emitted MR signal from the tissue. The RF coil of the scanner provides a more homogenous excitation, but deposits much higher RF power into the body in order to achieve the required excitation of the local tissue being imaged. Local coils can be used to excite the surrounding tissue, but the excitation is less homogenous and may result in a distorted image. To enable the imaging coils to be used in both the "receive only" mode and the "transmit\receive" mode, a switchable blocking circuitry is integrated into the apparatus. For "transmit\receive" mode the blocking circuit should be inactive, while for "receive only" mode, it should de-tune the imaging coil during RF transmit by the MR scanner RF coil 3. This is done by changing its resonant frequency and injecting a high impedance in the circuit to suppress the induction of any current.

Different methods may be used to block the imaging coil during RF transmit. FIG. 3 illustrates a simple and commonly used blocking circuit consisting of a high voltage rated PIN diode $D_1$ and an inductor $L_1$. As shown in FIG. 3, the inductor is placed in series with the diode and in parallel to the capacitor Cp. The inductor is tuned to resonate with capacitor Cp at the resonant frequency of the circuit (e.g., 42.6 MHz/Tesla). When the diode is activated, by a positive bias voltage supplied by the MR scanner on the center conductor of the coaxial cable, a short-circuit is created between the inputs to the imaging coil IC that has the effect of detuning the coil.

Using Equation 1 above, and knowing the capacitance Cp, the required inductance to detune the coil IC can be calculated. The blocking network can be tested by applying a DC bias voltage through the network analyzer. With the diode $D_1$ activated, the former resonance (at the frequency of the scanner) splits into two resonances, one at a much lower frequency, the other at a much higher frequency. By adjusting the inductor $L_1$, the location of these detuned resonances can be varied to achieve resonance frequencies far from the imaging frequency.

The Probe Construction

Figure 4:
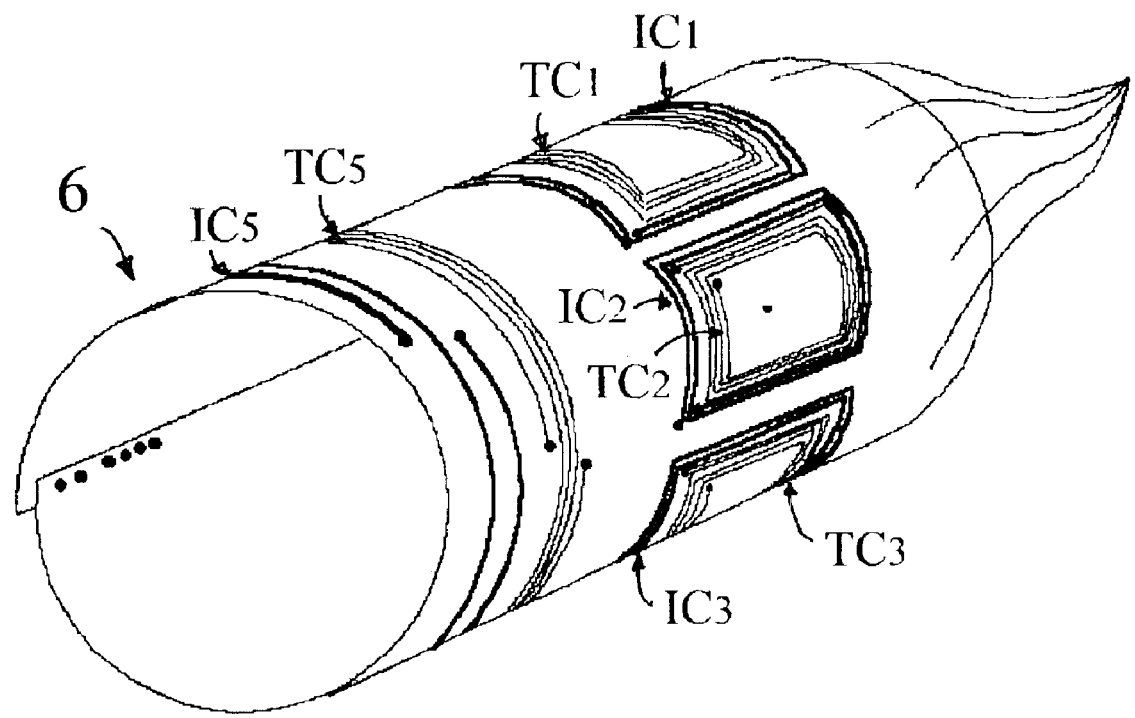
FIG. 4 illustrates one form of coil assembly, having a set of tracking coils and a set of imaging coils, included in the probe of the apparatus of FIG. 1.
Figure 5:
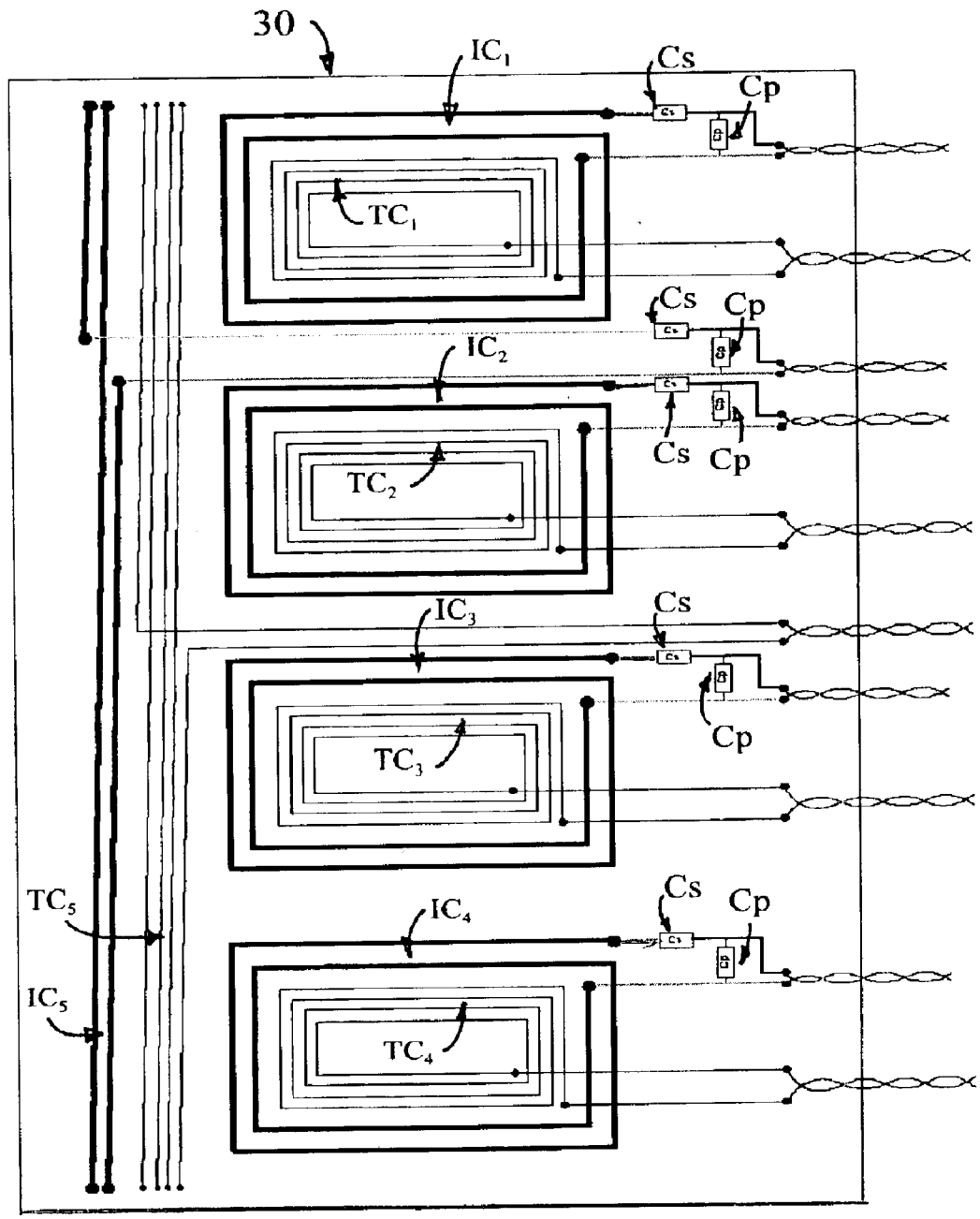
FIG. 5 illustrates a preferred manner of making the coil assembly of FIG. 3 using printed circuit techniques.

FIGS. 4 and 5 illustrate a preferred construction of the probe 6, particularly the construction of the coil assembly including the set of tracking coils $TC_X$–$TC_Z$ and imaging coils $IC_X$–$IC_Z$, and the method of making such a coil assembly. In this preferred construction of the probe 6, the coil assembly is made by printed circuit techniques, wherein electrically-conductive deposits are applied to a planar dielectric substrate, which is then formed into an annular shape with its opposite edges joined to each other. The electrically-conductive deposits as initially applied to the planar dielectric substrate are configured and located such that when the substrate is formed into the annular shape, the electrically-conductive deposits define the two sets of tracking coils $TC_X$–$TC_Z$ and imaging coils $IC_X$–$IC_Z$, respectively.

FIG. 5 illustrates the planar dielectric substrate, therein generally designated 30, including the various electrically-conductive deposits initially formed thereon, i.e., before the substrate is formed into an annular shape, in this case a cylindrical shape. In the preferred embodiment described below, the planar dielectric substrate 30 is of a flexible dielectric material such that it may be conveniently bent into the cylindrical shape and its opposite edges joined to define a hollow, cylindrical probe 6 integrally formed with the two sets of tracking coils $TC_X$–$TC_Z$ and imaging coils $IC_X$–$IC_Z$. The electrically-conductive deposits also include the appropriate electrical components, particularly capacitors, which are integrally formed with the coils in the cylindrical probe shown in FIG. 3.

As shown in FIG. 5, the planar dielectric substrate 30 is initially formed with electrically-conductive deposits defining five tracking coils $TC_1$–$TC_5$ when the substrate is bent into its cylindrical shape and its opposite ends joined, as shown in FIG. 4. Thus, the electrically-conductive deposits $TC_1$, $TC_3$ of FIG. 5 define one pair of orthogonal coils (e.g., corresponding to orthogonal coil $TC_X$, FIG. 1); the electrically-conductive deposits $TC_2$, $TC_4$ of FIG. 5 define a second pair of orthogonal coils (e.g., corresponding to orthogonal coil $TC_Y$, FIG. 1); and electrically-conductive deposit $TC_5$ in FIG. 5 defines a third orthogonal coil (e.g., corresponding to orthogonal coil $TC_Z$, FIG. 1). While FIGS. 4 and 5 illustrate the third orthogonal coil as consisting only of a single coil, it will be appreciated that the third orthogonal coil could also consist of a pair of orthogonal coils corresponding to, and straddling, orthogonal pairs $TC_1$, $TC_3$ and $TC_2$, $TC_4$, respectively.

The flexible dielectric substrate 30 is also initially formed, while in the planar state, with similar electrically-conductive deposits, shown as $IC_1$–$IC_5$, respectively, defining a pair of orthogonal coils (e.g., corresponding to orthogonal coil $IC_X$, FIG. 1); a pair of orthogonal coils (e.g., corresponding to orthogonal coil $IC_Y$, FIG. 1); and a single orthogonal coil (e.g., corresponding to orthogonal coil $IC_Z$, FIG. 1).

As shown in FIG. 5, the electrically-conductive deposits $TC_1$–$TC_4$ defining the two pairs of orthogonal tracking coils, and the electrically-conductive deposits $IC_1$–$IC_4$ defining the two pairs of imaging coils, are formed on the substrate 30 to extend parallel to each other along one (the horizontal) orthogonal axis of the substrate, and are spaced from each other along the other (the vertical) orthogonal axis. It will also be seen that the tracking coil deposits $TC_1$–$TC_4$ are formed within, and coaxial with respect to, the image coil deposits $IC_1$–$IC_4$, respectively. It will further be seen in FIG. 5 that the tracking coil deposits $TC_5$ and imaging coil deposits $IC_5$ are formed as parallel straight lines extending along the latter (vertical) axis of the substrate laterally of the deposits $TC_1$–$TC_4$ and $IC_1$–$IC_4$.

Thus, when the flexible substrate 30 is bent into its cylindrical shape and its opposite edges joined together, as shown in FIG. 4, deposits $TC_1$, $TC_3$ will define a first pair of orthogonal tracking coils; deposits $TC_2$, $TC_4$ will define a second pair of orthogonal tracking coils; deposits $TC_5$ will define a third orthogonal tracking coil; deposits $IC_1$, $IC_3$ will define a first pair of orthogonal imaging coils; deposits $IC_2$, $IC_4$ will define a second pair of orthogonal imaging coil; and deposits $IC_5$ will define a third orthogonal imaging coil. Each coil is connected to a pair of twisted wires, as shown in FIG. 5, to eliminate electromagnetic induction to the cable.

The two pairs of imaging coils defined by the electrically-conductive deposits $IC_1$, $IC_3$ and $IC_2$, $IC_4$, respectively, are in the form of saddle coils extending longitudinally of the probe 6; they provide radial sensitivity to the probe. The third orthogonal imaging coil defined by electrically-conductive deposit $IC_5$ extends transversely at the tip of the probe and provides a forward imaging capability to the probe. Thus, if the probe encounters a lesion to be examined, the endoscope can be pressed against the lesion "sidewise" or "tipwise" to enable a better examination of the lesion.

By thus combining this three-dimensional spatial coverage for imaging, with the tracking capability for indicating the location and orientation of the probe, the illustrated apparatus provides an extremely comprehensive imaging approach to investigating various lesions that may be encountered by the probe.

In addition, the use of a separate set of tracking coils for tracking purposes, and a separate set of imaging coils for imaging purposes, enables optimization of each set of coils for the specific task of the respective set. Thus, while the low-level gradient fields are best measured with multi-turn tracking coils, the need for low resistance of the imaging coils favors fewer-turn or single-turn imaging coils. This is clearly shown in FIGS. 4 and 5, wherein it will be seen that each of the tracking coils has a larger number of turns than each of the imaging coils.

Another advantage in the method of making the probe 6, in the manner illustrated in FIGS. 4 and 5, is that a hollow probe construction is produced, such as to define a through passageway. Such a passageway is useful, for example, for the insertion of a guide wire for the injection of a contrast material, or for the removal of a tissue sample (biopsy), according to the diagnostic or interventional procedure for which the described apparatus is to be used.

A still further advantage is that, by using printed circuit technology for making the coil assemblies described above with respect to FIGS. 4 and 5, highly accurate coil assemblies can be produced in volume and at relatively low cost.

Figure 6:
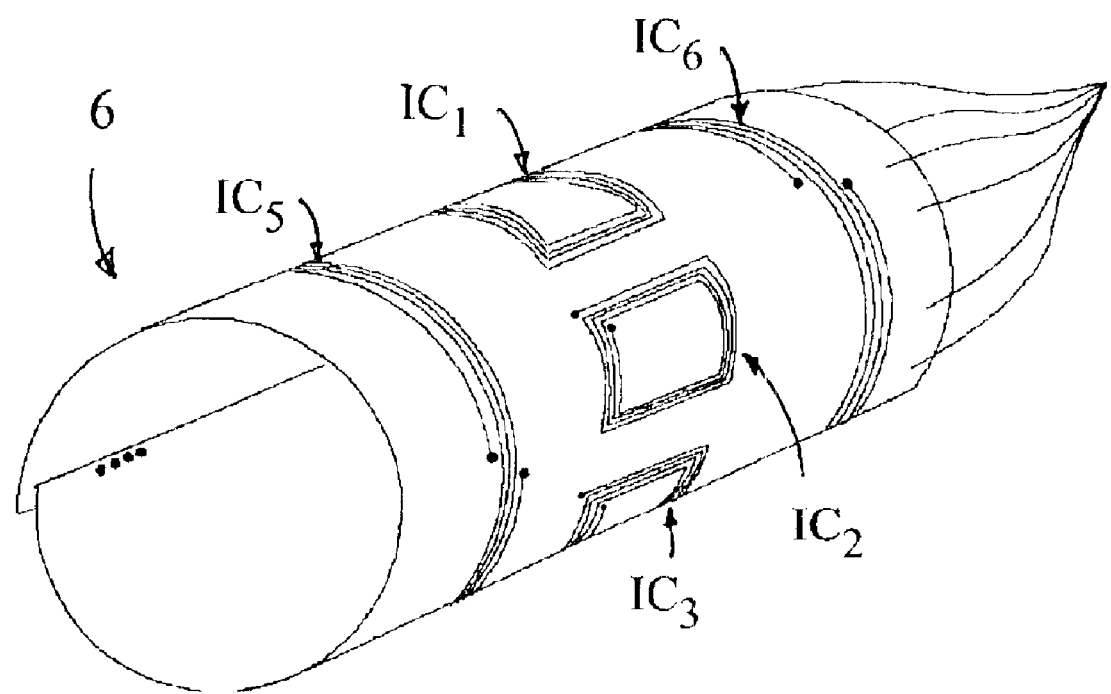
FIGS. 6 and 7 are views, corresponding to those of FIGS. 4 and 5, illustrating a variation in the construction of the coil assembly, these figures illustrating, for simplification purposes, only one set of the coils, rather than both sets.
Figure 7:
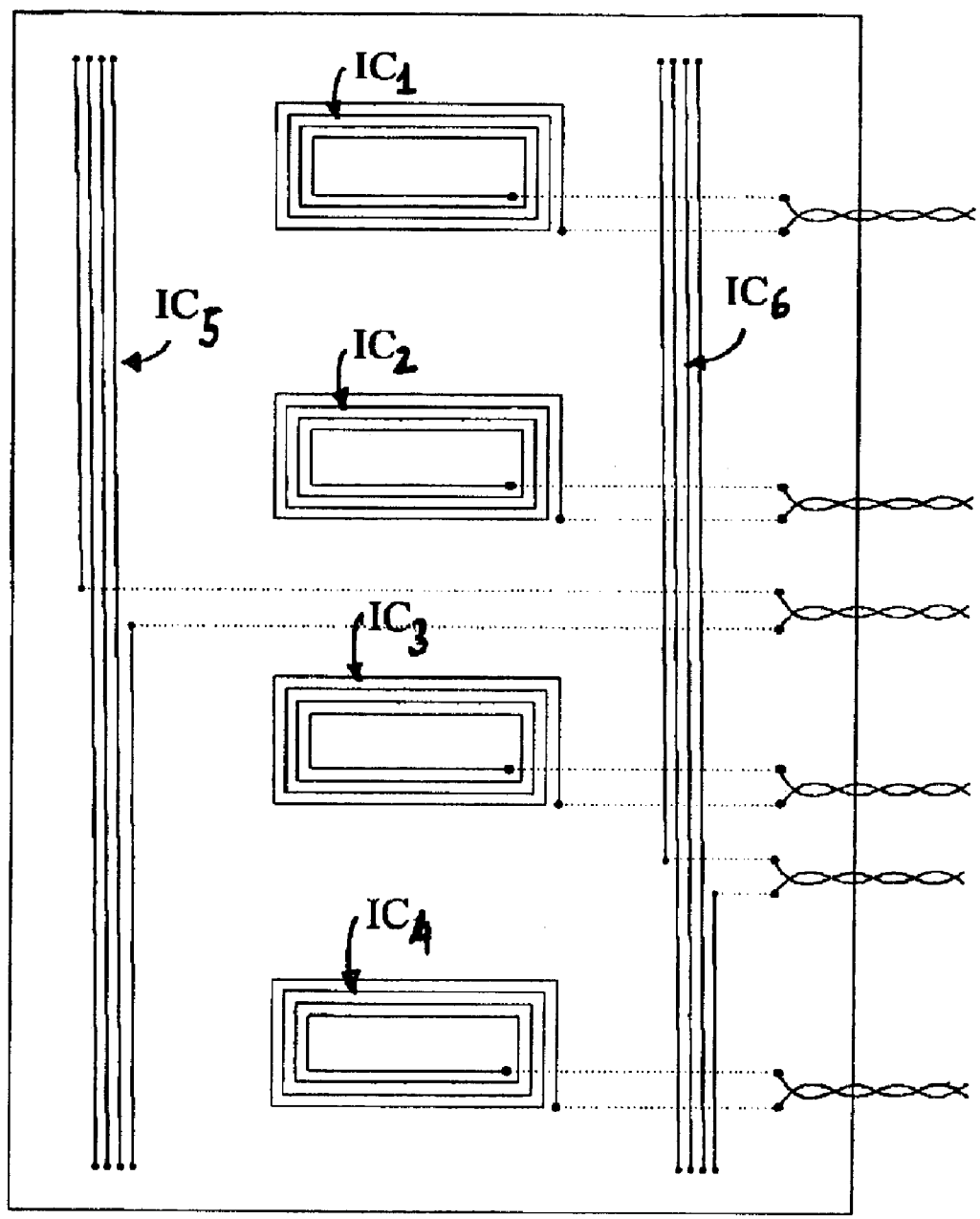

FIGS. 6 and 7 are views, corresponding to those of FIGS. 4 and 5, but illustrating the third (Z-axis) imaging coil, instead of being a single coil as in FIGS. 4 and 5, as also being in the form of a pair of coils, as shown at IC5, IC6 in FIG. 6, straddling the two pairs of saddle coils. For this purpose, there would be electrically-conductive deposits $IC_5$, $IC_6$, laterally on both sides of the electrically-conductive deposits defining the two pairs of orthogonal coils on the planar substrate 30, such that when the substrate is bent into its cylindrical form, such electrically-conductive deposits would define a pair of the Z-axis imaging coils.

While FIGS. 6 and 7 illustrate only the imaging coils, it will be appreciated that a similar construction would be provided for the electrically-conductive deposits defining the tracking coils.

Figure 8:
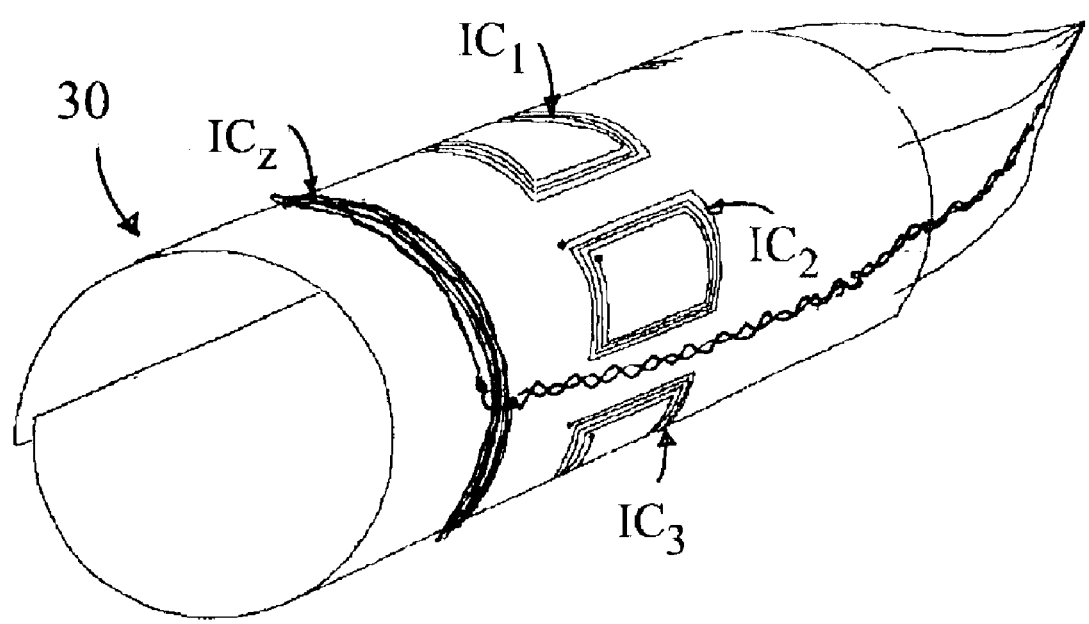
FIGS. 8 and 9 are views corresponding to those of FIGS. 6 and 7, but illustrating a further variation
Figure 9:
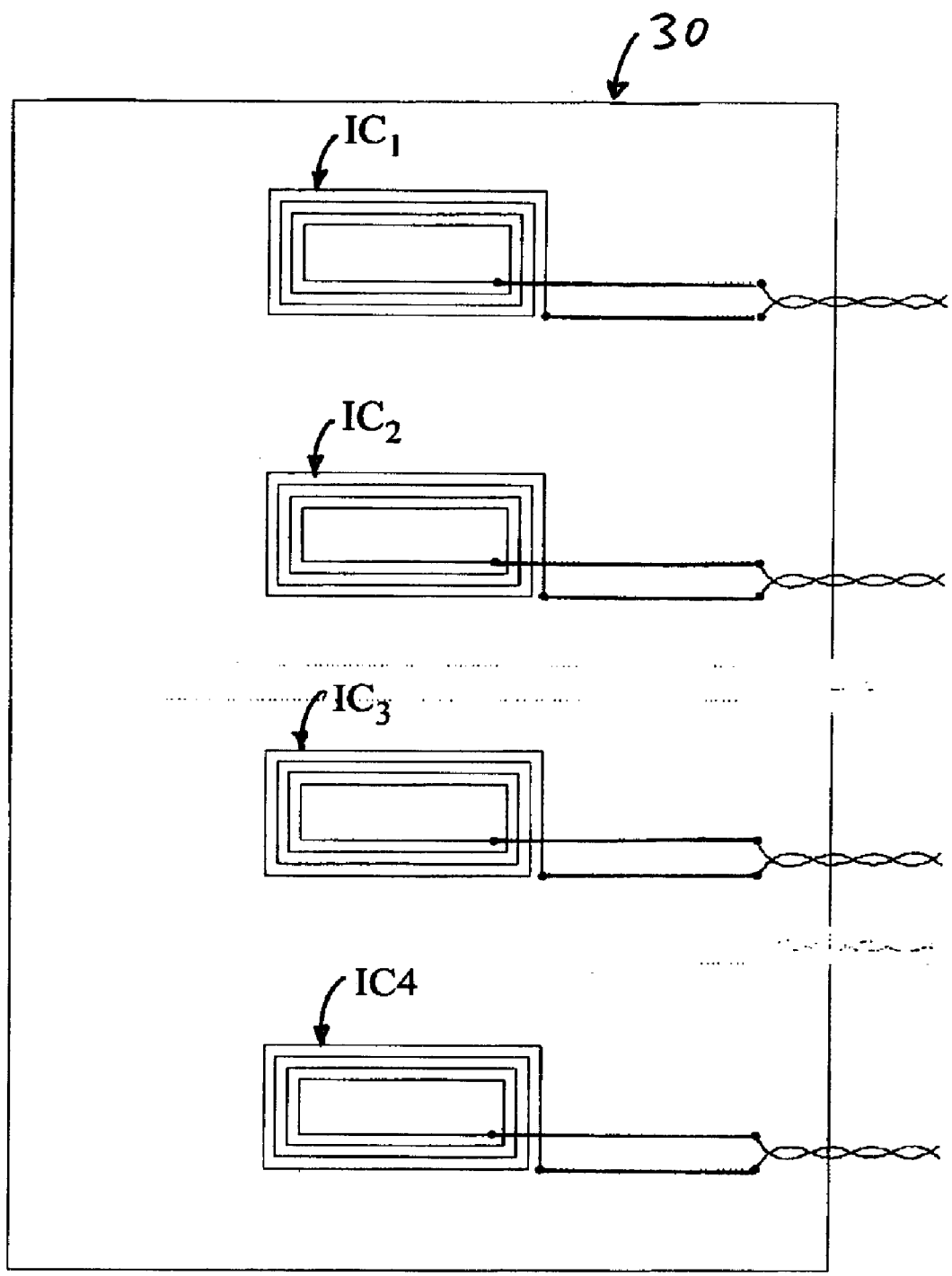

FIGS. 8 and 9 are views corresponding to those of FIGS. 6 and 7, but illustrating the above-described printed circuit technique used for producing only two pairs of orthogonal imaging coils (and similarly tracking coils, not shown in FIGS. 8 and 9). In this case, the dielectric substrate 30, in its planar state shown in FIG. 9, is not formed with the electrically-conductive deposits laterally of those defining the X-axis and Y-axis coils; but rather, after the dielectric has been bent into its cylindrical shape, the Z-axis coil, shown at $IC_Z$ in FIG. 8, is applied in the conventional manner by winding a coil around the cylindrical dielectric.

It will be appreciated that whereas only one set of coils is shown in FIGS. 8 and 9, this is only for simplification purposes, as the coil assembly, when produced for use in the system described above with respect to FIGS. 1 and 2, would preferably include a set of imaging coils as well as a set of tracking coils, as described above.

Figure 10:
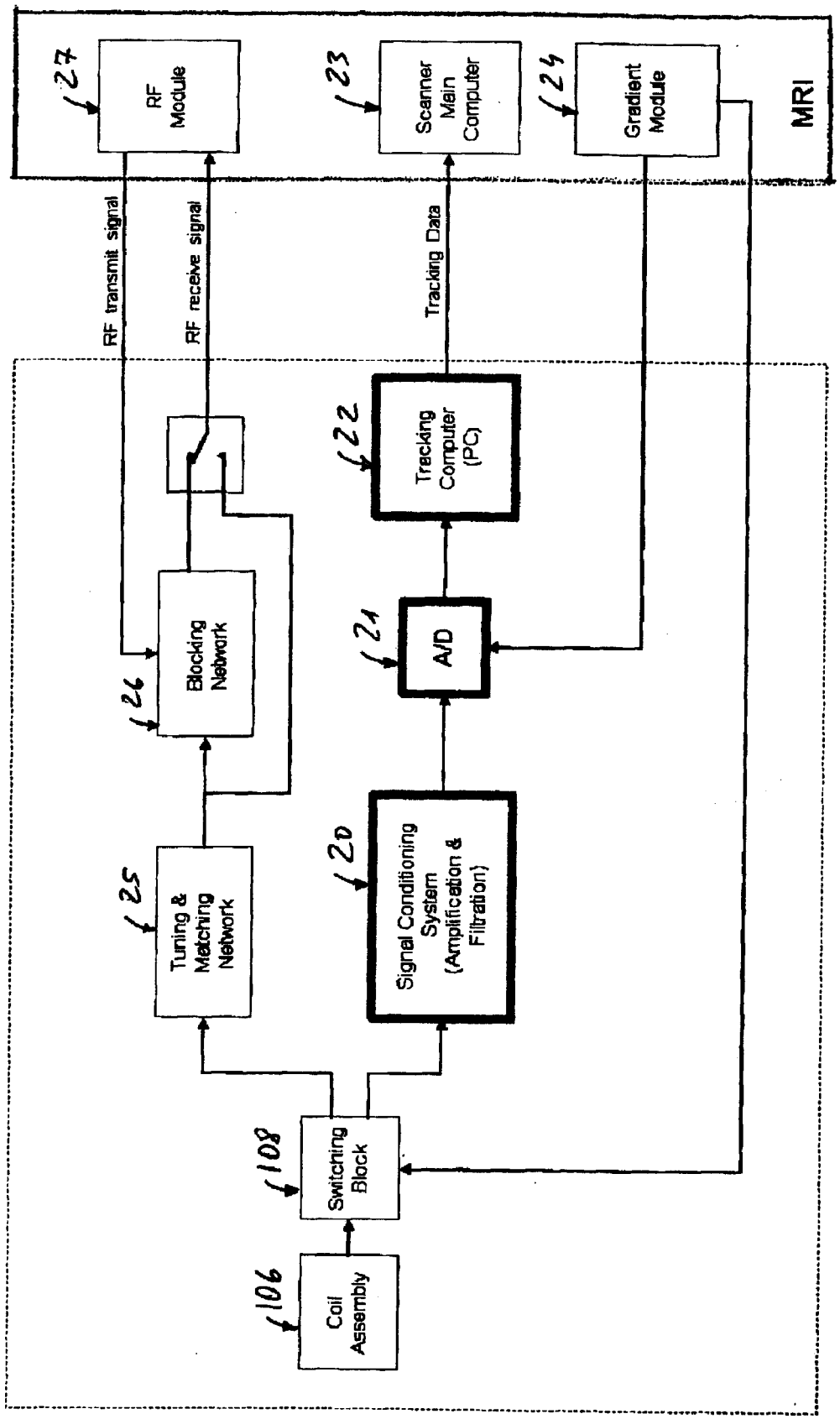
FIG. 10 is a block diagram corresponding to FIG. 2, but illustrating a possible modification in the apparatus.

However, it is contemplated that a simplified embodiment of the invention could use the same set of coils for both tracking and imaging. This is shown in FIG. 10 in which the coil assembly, therein designated 106, includes a single set of coils for use both for tracking and for imaging. As shown in FIG. 10, such a system would also include a switching block 108, which directs the signals induced in the coils of assembly 106 to the tracking sub-system (i.e. to the signal conditioning network 20) during gradient activation and deactivation, and to the imaging system (i.e. to the tuning and matching network 25) during the MR signal detection (the read-out gradient).

The system illustrated in FIG. 10 is otherwise substantially the same as described above with respect to FIG. 2.

The system illustrated in FIG. 10 may simplify the manufacturing of the probe since it requires only one set of coils. However, it may result with sub-optimal imaging, since the single set of coils cannot be optimized both for tracking and for imaging. Therefore, the previously-described embodiment, as illustrated in FIG. 2, is preferable since it does not require a compromise between the different requirements in using the coils for both tracking and imaging.

While the main magnetic field is shown in FIG. 1 as being generated by an electromagnetic coil (2), it will be appreciated that the main magnetic field could also be generated by a permanent magnet, or a superconducting magnet.

Preliminary Results:

To assess the potential advantages of the described combined tracking and imaging system a crude imaging coil was constructed and used to scan a simple phantom, as described below, using the matching and tuning circuit described above with respect to FIG. 3. For this preliminary test, the small coil was used as a transmit\receive coil, thus avoiding the need to construct the blocking circuitry. The imaging was done on a Signa-SP open scanner at the iMRI Department of the Norton Hospital, Louisville, Ky.

Figure 11:
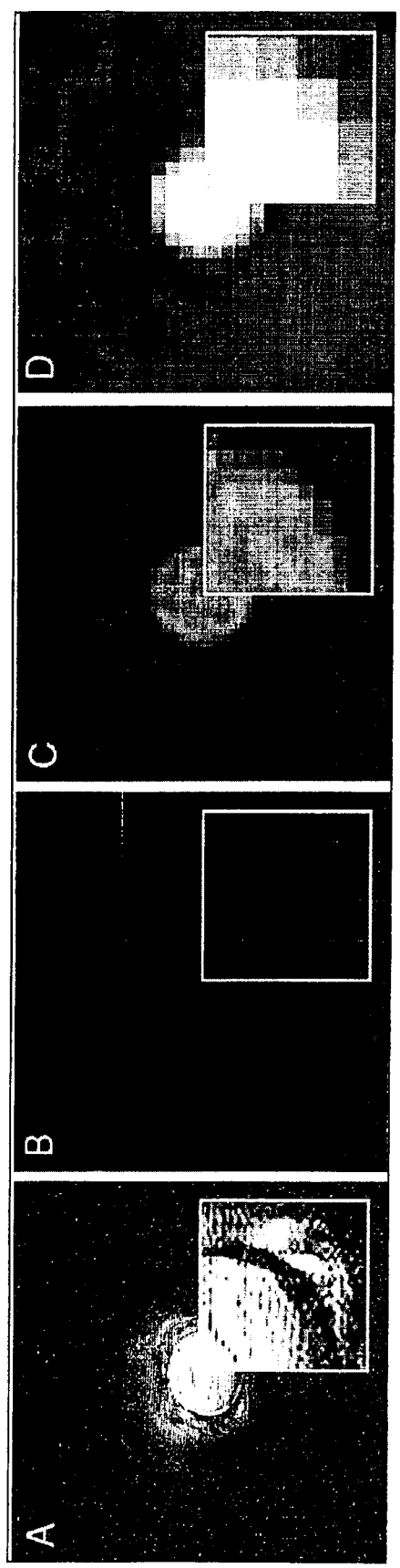
FIG. 11 illustrates experimental results produced in testing the tracking system.

The phantom consisted of a syringe filled with contrast agent (cupper sulphate, 20 mmol) placed inside a small cup filled with tap water. The imaging coil was placed around the syringe and was positioned at the level of the tip of the syringe shaft. The RF frequency of the scanner was fine-tuned in the pre-scan phase to achieve maximum response of the received signal. The prototype was used as a transmit\receive coil, using the smallest field of view (8×8 cm) and the highest resolution (512×512). Excellent signal to noise ratio, excellent contrast between the contrast agent and the surrounding water, and very high resolution of about 150 micron were obtained (FIG. 11A). As a comparison, an attempt was made to obtain an equivalent image using the same scan parameters, but imaging with an external body coil as a transmit/receive coil. As the signal intensity from the small voxel was below the noise floor of the scanner, no contrast between the contrast fluid and the water could be detected (FIG. 11B).

To achieve an image with an acceptable level of contrast, the image resolution had to be reduced to about 0.8 mm (FIG. 11C). To obtain an equivalent level of contrast as achieved with the local coil, the resolution had to be further reduced to about 2.0 mm (FIG. 11D). Although the image created with the local coil was slightly distorted, probably due to inhomogeneity of the transmit RF field, the superior contrast and the much higher resolution were well presented.

Figure 12:
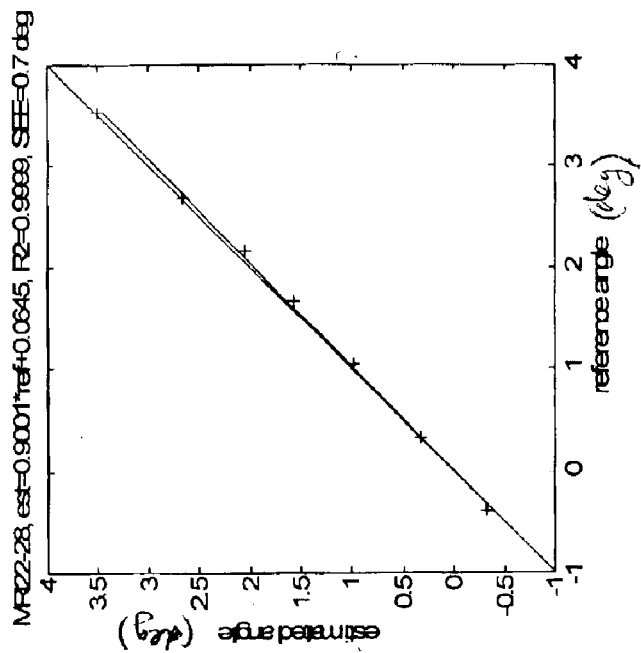
FIG. 12 illustrates experimental results demonstrating the accuracy of real time tracking: namely, the angular tracking accuracy (a) and the positional tracking accuracy (b).
Figure 12:
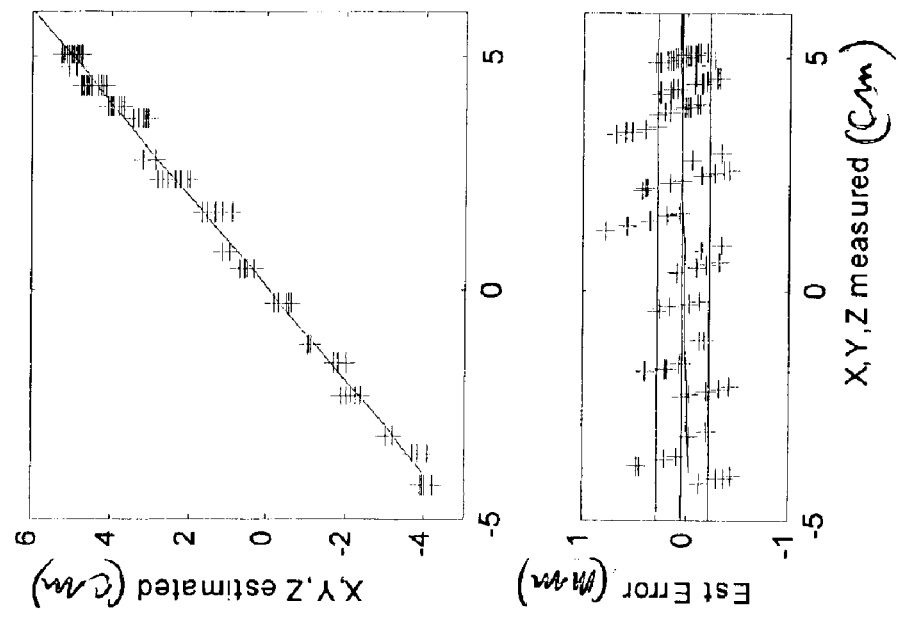

The tracking system was tested on a Signa CV/i close-bore scanner and on a Signa-SP open scanner. Simple integration to any MR scanner, realtime tracking with any imaging protocol and without changing the scan parameters (pulse sequence description, PSD), and high accuracy within the field of imaging were demonstrated on both scanners. The foregoing are shown in FIG. 12, wherein the upper curve (a) demonstrates the angular tracking accuracy, and the lower curve (b) indicates the positional tracking accuracy. In these tests, the location tracking error=0.6±0.7 mm; and the orientation tracking error=0.5±0.5 degrees.

Potential Clinical Applications

As indicated above, many clinical applications involving different endoscopic procedures can benefit from the combined use of visual inspection and MR imaging according to the present invention. The potential application of MR-enhanced GI endoscopy is presented merely as an illustrative example for EMRI.

Routine endoscopy is currently done with non-MR-compatible endoscopes and with no access to an MR scanner. Thus, gastrointestinal EMRI can become a second line procedure, following screening procedures like proctosigmoidoscopy or barium enema with positive findings, or standard colonoscopy with questionable finding. Although EMRI with close-bore scanners can benefit from their stronger magnetic fields, open scanners are expected to be the more appropriate setup for EMRI by providing better access to the patient. When a suspected lesion is identified during the optical endoscopy, the operator places the endoscope tip adjacent to the suspected lesion (e.g. the wall of the colon) and starts an interactive, multi-slice MR scan at the position of the tip and in transverse direction to the axis of the endoscope. Following this initial scan, additional high-resolution scans in different planes (radial, parallel or oblique scans) that cut through the suspected lesion can be defined by the operator with reference to initial "scout" radial images and to the tip of the endoscope. If the region of interest is larger than the spherical coverage of the receiving coils the operator can steer the endoscope along the region of interest, with realtime interactive scanning that provides a set of consecutive images that cut through the region of interest. The main properties that are required for this application, namely realtime tracking of the endoscope's tip and spherical coverage of the RF coils, are provided by the present invention.

While the invention has been described with respect to one preferred embodiment, it will be appreciated that this is set forth merely for purposes of example, and that many other variations, modifications and applications of the invention may be made.

BIBLIOGRAPHY

Albert J, Schilling D, Breer H, Jungius K P, Riemann J F, Adamek H E, Mucinous cystadenoma and intraductal papillary mucinous tumors of the pancreas in magnetic resonance cholangiopancreatography. Endoscopy 2000;32:472–6.

Atalar E, Bottomley P A, Ocali O, Correia L C, Kelemen M D, Lima J A, Zerhouni E A, High resolution intravascular MRI and MRS by using a catheter receiver coil. Magn Reson Med 1996; 36:596–605.

Atkin W S, Morson B C, Cuzick J, Long-term risk of colorectal cancer after excision of rectosigmoid adenomas. N Engl J Med 1992; 326:658–62.

Bond J H, The management of patients with colorectal polyps, Clinical Update, Vol. 1 No. 2 October 1993 ISSN 1070–7212.
(http://www.asge.org/gui/clinical_info/updates/cu_colorectal_polyps.asp)

Dumoulin C L, Souza S P, Darrow R D. Real-time position monitoring of invasive devices using magnetic resonance. Magn Reson Med. Mar. 29, 1993 (3): 411–5.

Feldman D R, Kulling D P, Hawes R H, Kay C L, Muckenfuss V R, Cotton P B, Bohning D E, Young J W, MR endoscopy: preliminary experience in human trials, Radiology 1997; 202:868–870.

Hildebrandt U, Feifel G. Importance of endoscopic ultrasonography in staging for treatment of rectal cancer. Gastrointest Endosc Clin N Am 1995;5:843–50.

Hogan W J, Stewart E T, Geenen J E, Dodds W J, Bjork J T, Leinicke J A. A prospective comparison of the accuracy of colonoscopy vs air-barium contrast exam for detection of colonic polypoid lesions. Gastrointest Endosc 1977;23:A230.

Hurst G C, Hua J, Duerk J L, Cohen A M, Intravascular (Catheter) NMR Receiver Probe: Preliminary Design Analysis and Application to Canine Iliofemoral Imaging, Magn Reson Med 1992; 24:343–357.

Kantor H L, Briggs R W, Balaban R S, In vivo 31P nuclear magnetic resonance measurements in canine heart using a catheter-coil, Circ Res 1984; 55:261–6.

Kulling D, Bohning D E, Kay C L, Feldman D R, Endoscopic magnetic resonance imaging at variable coil orientations, Endoscopy 1997, 29:336–337.

Kulling D, Feldman D R, Kay C L, Bohning D E, Hoffman B J, Van Velse A K, Baron P L, Lahr C J, Hawes R H. Local staging of anal and distal colorectal tumors with the magnetic resonance endoscope. Gastrointest Endosc 1998;47(2): 172–8.

Kulling D, Feldman D R, Kay C L, Hoffman B J, Reed C E, Young J W, Hawes R H. Local staging of esophageal cancer using endoscopic magnetic resonance imaging: prospective comparison with endoscopic ultrasound. Endoscopy 1998;30(9):745–9.

Lightdale C J. Diagnosis, staging, and cure of early gastrointestinal cancer [editorial]. Gastrointest Endosc 1996;44:95–6.

Lightdale C J. Esophageal cancer: practice guidelines. Am J Gastroenterol 1999;94:20–9.

Lotfi A M, Spencer R J, Ilstrup D M, Melton L J Ill. Colorectal polyps and the risk of subsequent carcinoma. Mayo Clin Proc 1986;61:33743.

Martin A J, Henkelman R M. Intravascular MR imaging in a porcine animal model. Magn Reson Med 1994; 32:224–9.

Martin A J, Plewes D B, Henkelman R M. MR imaging of blood vessels with an intravascular coil. J Magn Reson Imaging. 1992; 2:421–9.

Richter A, Gaa J, Niedergethmann M, George M, Trede M, Post S. Ultrafast magnetic resonance tomography changes the standard pancreas diagnosis. Chirurg 2001;72:697–703.

Rosch T, Lightdale C J, Botet J F, Boyce G A, Sivak M V Jr, Yasuda K, Heyder N, Palazzo L, Dancygier H, Schusdziarra V, et al. Localization of pancreatic endocrine tumors by endoscopic ultrasonography. N Engl J Med 1992; 326:1721–6.

Tada M, Inoue H, Yabata E, Okabe S, Endo M. Colonic mucosal resection using a transparent cap-fitted endoscope. Gastrointest Endosc 1996;44:63–5.

Tio, T L. Gastrointestinal TNM cancer staging by endosonography. New York: Igaku-Shoin; 1995.

Wiersema M J, Wiersema L M, Khusro Q, et al. Combined endosonography and fine needle aspiration cytology in the evaluation of gastrointestinal lesions. Gastrointest Endosc 1994; 40:199–206.

Winawer S J, Zauber A G, Gerdes H, et al. Reduction in colorectal cancer incidence following colonoscopic polypectomy: report from the National Polyp Study (NPS). Gastroenterology 1991; 100:A410.

Winawer S J, Fletcher R H, Miller L, et al. Colorectal cancer screening: clinical guideline and rationale. Gastroenterology 1997;112:594–642.

Yamada I, Saito N, Takeshita K, Yoshino N, Tetsumura A., Kumagai J, Shibuya H, Early gastric carcinoma: evaluation with high-spatial resolution MR imaging in vitro, Radiology 2001; 220:115–121.

What is claimed is:

1. Endoscopic examining apparatus for examining the interior of a body cavity, comprising:
 a probe movable through said body cavity;
 coil assembly including a plurality of coils carried by said probe, said coil assembly including at least one imaging coil and a separate set of at least two orthogonal tracking coils;
 and a control system for controlling said tracking coils to sense and indicate the location and orientation of said probe within said body cavity, and said imaging coil to image selected areas within said body cavity.

2. The apparatus according to claim 1, wherein said set of tracking coils includes at least two pairs of orthogonal coils.

3. The apparatus according to claim 1, wherein said at least one imaging coil includes two pairs of orthogonal coils extending longitudinally of the probe to provide radial sensitivity to the probe, and at least one additional coil extending transversally at the tip of the probe to provide a forward imaging capability to the probe.

4. The apparatus according to claim 1, wherein said set of tracking coils includes two pairs of orthogonal coils extending longitudinally of the probe, and a third pair of orthogonal coils extending transversely of the probe to provide three-dimensional sensitivity to the tracking coils.

5. The apparatus according to claim 1, wherein each of said tracking coils has a larger number of turns than each of said imaging coils.

6. The apparatus according to claim 1, wherein each of said tracking coils is coaxial with one of said imaging coils.

7. The apparatus according to claim 1, wherein:
 said apparatus is an MRI apparatus having gradient coils for generating gradient electromagnetic fields in an imaging space occupied by the probe within the body cavity;
 said imaging coil is controlled by said control system for imaging said selected areas within the body cavity;
 and said tracking coils are controlled by said control system to sense the instantaneous electromagnetic field within said imaging space and, thereby, to indicate the location and orientation of the probe within said body cavity.

8. The apparatus according to claim 1, wherein said probe is of a hollow construction and defines a continuous passageway therethrough.

9. The apparatus according to claim 1, wherein said coils are carried by at least one planar dielectric substrate which is formed into an annular configuration.

10. The apparatus according to claim 9, wherein said dielectric substrate is flexible and is flexed into a cylindrical configuration.

11. MRI apparatus for examining the interior of a body cavity, comprising:
 means for providing a main magnetic field through the body cavity to be examined;
 a plurality of gradient coils for generating gradient electromagnetic fields within said body cavity;
 a probe movable through said body cavity and carrying a coil assembly including a set of at least two orthogonal tracking coils and at least one imaging coil;
 and a control system for controlling said gradient coils to generate said gradient electromagnetic field, said tracking coils to sense and indicate the location and orientation of said probe within said body cavity, and said at least one imaging coil to image selected areas within said body cavity.

12. The MRI apparatus according to claim 11, wherein said probe includes a separate set of at least two orthogonal imaging coils.

13. The MRI apparatus according to claim 12, wherein each of said sets of coils carried by said probe includes at least two pairs of orthogonal coils.

14. The MRI apparatus according to claim 12, wherein said set of imaging coils carried by said probe includes two pairs of orthogonal coils extending longitudinally of the probe to provide radial sensitivity to the probe, and at least one additional coil extending transversally at the tip of the probe to provide a forward imaging capability to the probe.

15. The MRI apparatus according to claim 11, wherein said set of tracking coils carried by said probe includes two pairs of orthogonal coils extending longitudinally of the probe, and a third pair of orthogonal coils extending transversely of the probe to provide three-dimensional sensitivity to the tracking coils.

16. The MRI apparatus according to claim 11, wherein said probe and said tracking and imaging coils carried thereby, are of a hollow construction and define a continuous passageway therethrough.

17. The MRI apparatus according to claim 11, wherein each of said tracking coils has a larger number of turns than said imaging coil.

18. The MRI apparatus according to claim 11, wherein each of said tracking coils is coaxial with an imaging coil.

19. The MRI apparatus according to claim 11, wherein said tracking and imaging coils are carried by at least one dielectric substrate which is formed into an annular configuration.

20. The MRI apparatus according to claim 19, wherein said dielectric substrate is flexible and is flexed into a cylindrical configuration.

21. A probe movable within a body cavity for examining the interior of selected areas thereof; said probe comprising:
 a set of tracking coils including at least two orthogonal coils constructed and oriented on said probe to sense the location and orientation of the probe when moved within the body cavity;

and a set of imaging coils including at least two orthogonal coils constructed and oriented to image selected areas within the body cavity.

22. The probe according to claim 21, wherein each of said sets of coils includes at least two pairs of orthogonal coils.

23. The probe according to claim 21, wherein said set of imaging coils includes two pairs of orthogonal coils extending longitudinally of the probe to provide radial sensitivity to the probe, and at least one additional coil extending transversally at the tip of the probe to provide a forward imaging capability to the probe.

24. The probe according to claim 21, wherein said set of tracking coils includes two pairs of orthogonal coils extending longitudinally of the probe, and a third pair of orthogonal coils extending transversely of the probe to provide three-dimensional sensitivity to the tracking coils.

25. The probe according to claim 21, wherein said probe is of a hollow construction and defines a continuous passageway therethrough for insertion of a guidewire, for injection of a contrast material, for removal of a tissue sample, or for other purpose.

26. The probe according to claim 21, wherein each of said tracking coils has a larger number of turns than each of said imaging coils.

27. The probe according to claim 21, wherein each of said tracking coils is coaxial with one of said imaging coils.

28. The probe according to claim 21, wherein said tracking and imaging coils are carried by at least one, dielectric substrate which is formed into an annular configuration.

29. The probe according to claim 28 wherein said dielectric substrate is flexible and is flexed into a cylindrical configuration.

30. Endoscopic examining apparatus for examining the interior of a body cavity, comprising:

a probe movable through said body cavity;

a coil assembly including a plurality of coils carried by said probe;

and a control system for controlling the coils in said assembly to sense and indicate the location and orientation of said probe within said body cavity, and also to image selected areas within said body cavity;

wherein said coils are carried by at least one dielectric substrate which is formed into an annular configuration.

31. The apparatus according to claim 30, wherein said dielectric substrate is flexible and is flexed into a cylindrical configuration.

32. Endoscopic examining apparatus for examining the interior of a body cavity, comprising:

a probe movable through said body cavity;

a coil assembly including a plurality of coils carried by said probe;

and a control system for controlling the coils in said assembly to sense and indicate the location and orientation of said probe within said body cavity, and also to image selected areas within said body cavity;

wherein said coil assembly includes a single set of coils; and wherein said control system includes a tracking sub-system, an imaging sub-system, and a switching circuit for selectively utilizing said single set of coils for sensing and indicating the location and orientation of said probe within said body cavity, and also for imaging selected areas within said body cavity.

33. The apparatus according to claim 32, wherein said probe is of a hollow construction and defines a continuous passageway therethrough.

34. The apparatus according to claim 32, wherein said coils are carried by at least one dielectric substrate which is formed into an annular configuration.

35. The apparatus according to claim 34, wherein said dielectric substrate is flexible and is flexed into a cylindrical configuration.

* * * * *